(12) United States Patent
Fetvedt et al.

(10) Patent No.: US 8,430,257 B2
(45) Date of Patent: *Apr. 30, 2013

(54) DISSOLUTION TEST VESSEL WITH INTEGRAL VERTICALITY CONTROL

(75) Inventors: Jeremy Fetvedt, Raleigh, NC (US); Deon Smit, Cary, NC (US)

(73) Assignee: Agilent Technologies, Inc., Santa Clara, CA (US)

( * ) Notice: Subject to any disclaimer, the term of this patent is extended or adjusted under 35 U.S.C. 154(b) by 646 days.

This patent is subject to a terminal disclaimer.

(21) Appl. No.: 12/572,126

(22) Filed: Oct. 1, 2009

(65) Prior Publication Data

US 2011/0079096 A1    Apr. 7, 2011

(51) Int. Cl.
| | |
|---|---|
| G01N 33/00 | (2006.01) |
| B01L 3/14 | (2006.01) |
| B65D 21/02 | (2006.01) |
| B21D 39/06 | (2006.01) |
| G01N 33/15 | (2006.01) |

(52) U.S. Cl.
USPC ............ 220/23.87; 29/428; 73/866; 220/476; 220/737

(58) Field of Classification Search ............ 29/428, 29/434; 73/866; 220/23.87, 23.89, 476, 220/478, 480, 737
See application file for complete search history.

(56) References Cited

U.S. PATENT DOCUMENTS

| | | | | |
|---|---|---|---|---|
| 1,099,603 | A * | 6/1914 | Smith | 220/23.87 X |
| 1,187,498 | A * | 6/1916 | Knight | 220/23.89 X |
| 1,268,017 | A * | 5/1918 | Castle | 220/23.87 X |
| 1,283,580 | A * | 11/1918 | Ingersoll | 220/23.87 X |
| 2,750,264 | A * | 6/1956 | MacDougall | 422/205 |
| 2,765,832 | A * | 10/1956 | Tupper | 366/341 |
| 5,403,090 | A | 4/1995 | Hofer et al. | |
| 5,589,649 | A | 12/1996 | Brinker et al. | |
| 6,303,909 | B1 | 10/2001 | Fernando et al. | |
| 6,562,301 | B1 | 5/2003 | Dean et al. | |
| 6,673,319 | B2 | 1/2004 | Dean et al. | |
| 6,727,480 | B2 | 4/2004 | Fernando et al. | |
| 6,962,674 | B2 | 11/2005 | Dean et al. | |
| 7,395,726 | B2 * | 7/2008 | Sekizawa et al. | 73/866 |
| 7,891,516 | B2 * | 2/2011 | Takahashi | 220/62.22 |
| 7,938,032 | B2 * | 5/2011 | Fernando | 73/866 X |
| 2009/0207691 | A1* | 8/2009 | Fetvedt | 366/220 |
| 2009/0208373 | A1* | 8/2009 | Fetvedt | 73/866 X |
| 2009/0208377 | A1* | 8/2009 | Fetvedt | 29/428 X |
| 2010/0126980 | A1* | 5/2010 | Fetvedt | 29/428 X |
| 2011/0120239 | A1* | 5/2011 | Fetvedt | 73/866 |

* cited by examiner

*Primary Examiner* — Thomas P Noland

(57) ABSTRACT

A vessel includes a cylindrical section coaxially disposed about a central axis of the vessel. The cylindrical section includes an inside vessel surface, an outside vessel surface opposing the inside vessel surface, an upper end region circumscribing a vessel opening, and a lower end region axially spaced from the upper end region. A bottom section is disposed at the lower end region. A flange is coaxially disposed about the central axis and extends radially outward from the outside vessel surface at the upper end region. The flange includes a bottom surface facing generally toward the lower end region and perpendicular to the inside vessel surface. A ring may be coaxially disposed about the central axis and provide the bottom surface. An annular shoulder may protrude from the outside vessel surface, and may be spaced from or integrally adjoined to the flange.

20 Claims, 7 Drawing Sheets

DISSOLUTION TEST VESSEL WITH INTEGRAL VERTICALITY CONTROL

FIELD OF THE INVENTION

The present invention relates generally to dissolution testing of analyte-containing media. More particularly, the present invention relates to the centering and alignment of a vessel utilized to contain dissolution media with respect to an aperture in which the vessel is mounted or an instrument inserted in the vessel.

BACKGROUND OF THE INVENTION

Dissolution testing is often performed as part of preparing and evaluating soluble materials, particularly pharmaceutical dosage forms (e.g., tablets, capsules, and the like) consisting of a therapeutically effective amount of active drug carried by an excipient material. Typically, dosage forms are dropped into test vessels that contain dissolution media of a predetermined volume and chemical composition. For instance, the composition may have a pH factor that emulates a gastrointestinal environment. Dissolution testing can be useful, for example, in studying the drug release characteristics of the dosage form or in evaluating the quality control of the process used in forming the dose. To ensure validation of the data generated from dissolution-related procedures, dissolution testing is often carried out according to guidelines approved or specified by certain entities such as United States Pharmacopoeia (USP), in which case the testing must be conducted within various parametric ranges. The parameters may include dissolution media temperature, the amount of allowable evaporation-related loss, and the use, position and speed of agitation devices, dosage-retention devices, and other instruments operating in the test vessel.

As a dosage form is dissolving in the test vessel of a dissolution system, optics-based measurements of samples of the solution may be taken at predetermined time intervals through the operation of analytical equipment such as a spectrophotometer. The analytical equipment may determine analyte (e.g. active drug) concentration and/or other properties. The dissolution profile for the dosage form under evaluation—i.e., the percentage of analytes dissolved in the test media at a certain point in time or over a certain period of time—can be calculated from the measurement of analyte concentration in the sample taken. In one specific method employing a spectrophotometer, sometimes referred to as the sipper method, dissolution media samples are pumped from the test vessel(s) to a sample cell contained within the spectrophotometer, scanned while residing in the sample cell, and in some procedures then returned to the test vessel(s). In another more recently developed method, sometimes referred to as the in situ method, a fiber-optic "dip probe" is inserted directly in a test vessel. The dip probe includes one or more optical fibers that communicate with the spectrophotometer. In the in situ technique, the spectrophotometer thus does not require a sample cell as the dip probe serves a similar function. Measurements are taken directly in the test vessel and thus optical signals rather than liquid samples are transported between the test vessel and the spectrophotometer via optical fibers.

The apparatus utilized for carrying out dissolution testing typically includes a vessel plate having an array of apertures into which test vessels are mounted. When the procedure calls for heating the media contained in the vessels, a water bath is often provided underneath the vessel plate such that each vessel is at least partially immersed in the water bath to enable heat transfer from the heated bath to the vessel media. In one exemplary type of test configuration (e.g., USP-NF Apparatus 1), a cylindrical basket is attached to a metallic drive shaft and a pharmaceutical sample is loaded into the basket. One shaft and basket combination is manually or automatically lowered into each test vessel mounted on the vessel plate, and the shaft and basket are caused to rotate. In another type of test configuration (e.g., USP-NF Apparatus 2), a blade-type paddle is attached to each shaft, and the pharmaceutical sample is dropped into each vessel such that it falls to the bottom of the vessel. When proceeding in accordance with the general requirements of Section <711> (Dissolution) of USP24-NF19, each shaft must be positioned in its respective vessel so that its axis is not more than 2 mm at any point from the vertical axis of the vessel.

It is therefore a criterion in certain uses of vessels in which instruments operate that the vessel, and especially its inner surfaces, be aligned concentrically with respect to the instrument. Various approaches have been taken to assist in meeting this criterion, including those disclosed in U.S. Pat. No. 5,403,090, U.S. Pat. No. 6,562,301, U.S. Pat. No. 6,673,319, all assigned to the assignee of the present disclosure. Another approach to vessel alignment is disclosed in U.S. Pat. No. 5,589,649. Yet another approach to vessel alignment is the EaseAlign™ vessel centering ring commercially available from Varian, Inc., Palo Alto, Calif. Such approaches have not focused on the effect that the verticality of the vessel has on concentricity and alignment. In the present context, "verticality" generally refers to the precision with which the inside surface of the vessel is truly vertical, or the degree to which the inside surface is truly parallel with the central axis of the vessel or with an elongated instrument inserted into the vessel along the central axis. Regardless of the means taken to ensure that the vessel is concentrically positioned within the aperture of a vessel plate in which the vessel is mounted, if the vessel is not accurately vertical than it is still not aligned accurately. As a result, the inside surface of the vessel will not be precisely parallel with a shaft-based instrument that is intended to be inserted along the central axis of the vessel, and the radial distance between the shaft and the inside surface of the vessel will vary at different elevational points along the vertical axis.

Accordingly, there is a need for ensuring the verticality of a vessel when mounted in a vessel supporting structure such as is included in a dissolution testing apparatus.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a vessel includes a cylindrical section coaxially disposed about a central axis of the vessel, the cylindrical section, a bottom section and a flange. The cylindrical section includes an inside vessel surface, an outside vessel surface opposing the inside vessel surface, an upper end region circumscribing a vessel opening, and a lower end region axially spaced from the upper end region. The bottom section is disposed at the lower end region. The flange is coaxially disposed about the central axis. The flange includes a main flange portion extending radially outward from the outside vessel surface at the upper end region, and a bottom surface facing generally toward the lower end region and perpendicular to the inside vessel surface. The bottom surface lies in a horizontal plane and is entirely coplanar with the horizontal plane.

According to another implementation, the vessel further includes a shoulder coaxially disposed about the central axis at the upper end region and integrally adjoining the flange. The shoulder extends radially outward from the outside vessel surface and is located axially between the flange and the lower end region. The shoulder includes an outside shoulder surface concentric with the inside vessel surface relative to the central axis and perpendicular to the bottom surface.

According to another implementation, a vessel includes a cylindrical section coaxially disposed about a central axis of the vessel. The cylindrical section includes an inside vessel surface, an outside vessel surface opposing the inside vessel surface, an upper end region circumscribing a vessel opening, and a lower end region axially spaced from the upper end region. A bottom section is disposed at the lower end region. A flange is coaxially disposed about the central axis and extending radially outward from the outside vessel surface at the upper end region. The flange includes a bottom flange side facing generally toward the lower end region. A ring is coaxially disposed about the central axis and extends axially downward from the bottom flange side. The ring includes a bottom ring surface perpendicular to the inside vessel surface.

According to another implementation, a shoulder is coaxially disposed about the central axis at the upper end region. The shoulder extends radially outward from the outside vessel surface and is located axially between the flange and the lower end region. The shoulder includes an outside shoulder surface concentric with the inside vessel surface relative to the central axis.

According to another implementation, a dissolution test apparatus is provided. The dissolution test apparatus includes a vessel support member including a top surface and an inside edge circumscribing an aperture. A vessel extends through the aperture. The vessel includes a cylindrical section, a bottom section, a flange, and a ring. The cylindrical section is coaxially disposed about a central axis of the vessel. The cylindrical section includes an inside vessel surface, an outside vessel surface opposing the inside vessel surface, an upper end region circumscribing a vessel opening, and a lower end region axially spaced from the upper end region. The bottom section is disposed at the lower end region. The flange is coaxially disposed about the central axis and extends radially outward from the outside vessel surface at the upper end region. The flange includes a bottom flange side facing generally toward the lower end region. The ring is coaxially disposed about the central axis and extends axially downward from the bottom flange side. The ring includes a bottom ring surface perpendicular to the inside vessel surface, wherein the inside vessel surface is parallel to the inside edge of the vessel support member.

According to another implementation of the dissolution test apparatus, a shoulder is coaxially disposed about the central axis at the upper end region. The shoulder extends radially outward from the outside vessel surface and is located axially between the flange and the lower end region. The shoulder includes an outside shoulder surface concentric with the inside vessel surface relative to the central axis. The outside shoulder surface abuts the inside edge of the aperture.

According to another implementation, a method is provided for centering a vessel in an aperture of a vessel support member of a dissolution test apparatus, the aperture being coaxial with a vertical axis running through a center of the aperture. The vessel is inserted through the aperture. The vessel includes an inside vessel surface coaxially disposed about a central axis of the vessel, an outside vessel surface, a flange extending radially outward from the outside vessel surface, and a bottom surface extending axially downward from the flange and perpendicular to the inside vessel surface. The vessel is supported in a vertical orientation relative to the aperture by placing the bottom surface on a top surface of the vessel support member, wherein the entire inside vessel surface is parallel with the vertical axis.

According to another implementation, the vessel further includes an annular shoulder protruding radially outward from the outside vessel surface, the annular shoulder including an outside shoulder surface concentric with the inside vessel surface relative to the central axis. The position of the vessel is fixed relative to the aperture at an elevation at which the outside shoulder surface abuts an inside edge of the vessel support member circumscribing the aperture, wherein the central axis of the vessel is aligned with the vertical axis at any polar position relative to the vertical axis.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION OF THE INVENTION

Figure 1:
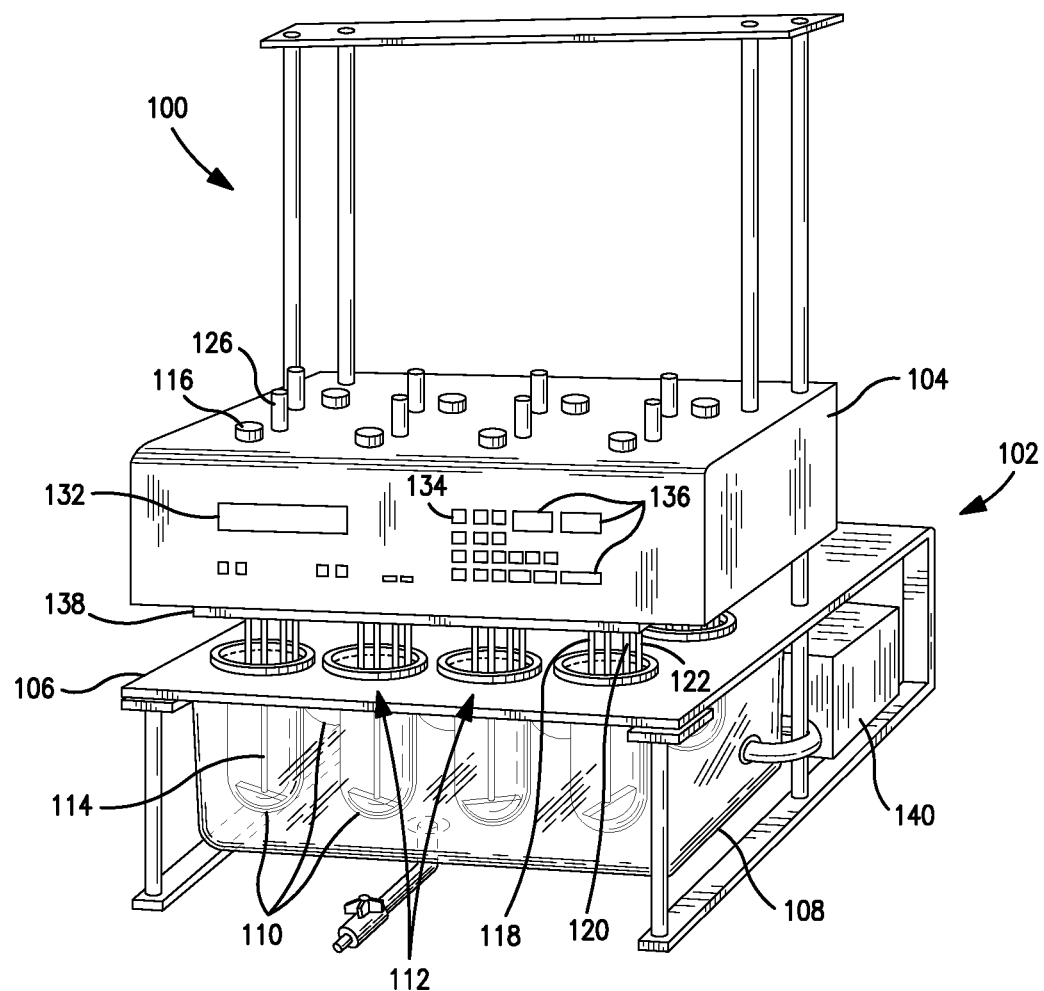
FIG. 1 is a perspective view of an example of a dissolution test apparatus with which vessels taught in the present disclosure may be utilized.

FIG. 1 is a perspective view of an example of a dissolution test apparatus 100 according to an implementation of the present disclosure. The dissolution test apparatus 100 may include a frame assembly 102 supporting various components such as a main housing, control unit or head assembly 104, a vessel support member (e.g., a plate, rack, etc.) 106 below the head assembly 104, and a water bath container 108 below the vessel support member 106. The vessel support member 106 supports a plurality of vessels 110 extending into the interior of the water bath container 108. FIG. 1 illustrates eight vessels 110 by example, but it will be understood that more or less vessels 110 may be provided. The vessels 110 may be centered in place on the vessel support member 106 at a plurality of vessel mounting sites 112 in a manner described in detail below. Vessel covers (not shown) may be provided to prevent loss of media from the vessels 110 due to evaporation, volatility, etc. Optionally, the vessel covers may be coupled to the head assembly 104 and movable by motorized means into position over the upper openings of the vessels 110, as disclosed for example in U.S. Pat. No. 6,962,674, assigned to the assignee of the present disclosure. Water or other suitable heat-carrying liquid medium may be heated and circulated through the water bath container 108 by means such as an external heater and pump module 140, which may be included as part of the dissolution test apparatus 100. Alternatively, the dissolution test apparatus 100 may be a waterless heating design in which each vessel 110 is directly heated by some form of heating element disposed in thermal contact with the wall of the vessel 110, as disclosed for example in U.S. Pat. Nos. 6,303,909 and 6,727,480, assigned to the assignee of the present disclosure.

The head assembly 104 may include mechanisms for operating or controlling various components that operate in the vessels 110 (in situ operative components). For example, the head assembly 104 typically supports stifling elements 114 that include respective motor-driven spindles and paddles operating in each vessel 110. Individual clutches 116 may be provided to alternately engage and disengage power to each stifling element 114 by manual, programmed or automated means. The head assembly 104 also includes mechanisms for driving the rotation of the stifling elements 114. The head assembly 104 may also include mechanisms for operating or controlling media transport cannulas that provide liquid flow paths between liquid lines and corresponding vessels 110. In the present context, the term "between" encompasses a liquid flow path directed from a liquid line into a vessel 110 or a liquid flow path directed from a vessel 110 into a liquid line. Accordingly, the media transport cannulas may include media dispensing cannulas 118 for dispensing media into the vessels 110 and media aspirating cannulas 120 for removing media from the vessels 110. The head assembly 104 may also include mechanisms for operating or controlling other types of in situ operative components 122 such as fiber-optic probes for measuring analyte concentration, temperature sensors, pH detectors, dosage form holders (e.g., USP-type apparatus such as baskets, nets, cylinders, etc.), video cameras, etc. A dosage delivery module 126 may be utilized to preload and drop dosage units (e.g., tablets, capsules, or the like) into selected vessels 110 at prescribed times and media temperatures. Additional examples of mechanisms for operating or controlling various in situ operative components are disclosed for example in above-referenced U.S. Pat. No. 6,962,674.

The head assembly 104 may include a programmable systems control module for controlling the operations of various components of the dissolution test apparatus 100 such as those described above. Peripheral elements may be located on the head assembly 104 such as an LCD display 132 for providing menus, status and other information; a keypad 134 for providing user-inputted operation and control of spindle speed, temperature, test start time, test duration and the like; and readouts 136 for displaying information such as RPM, temperature, elapsed run time, vessel weight and/or volume, or the like.

The dissolution test apparatus 100 may further include one or more movable components for lowering operative components 114, 118, 120, 122 into the vessels 110 and raising operative components 114, 118, 120, 122 out from the vessels 110. The head assembly 104 may itself serve as this movable component. That is, the entire head assembly 104 may be actuated into vertical movement toward and away from the vessel support member 106 by manual, automated or semi-automated means. Alternatively or additionally, other movable components 138 such as a driven platform may be provided to support one or more of the operative components 114, 118, 120, 122 and lower and raise the components 114, 118, 120, 122 relative to the vessels 110 at desired times. One type of movable component may be provided to move one type of operative component (e.g., stirring elements 114) while another type of movable component may be provided to move another type of operative component (e.g., media dispensing cannulas 118 and/or media aspirating cannulas 120). Moreover, a given movable component may include means for separately actuating the movement of a given type of operative component 114, 118, 120, 122. For example, each media dispensing cannula 118 or media aspirating cannula 120 may be movable into and out from its corresponding vessel 110 independently from the other cannulas 118 or 120.

The media dispensing cannulas 118 and the media aspirating cannulas 120 communicate with a pump assembly (not shown) via fluid lines (e.g., conduits, tubing, etc.). The pump assembly may be provided in the head assembly 104 or as a separate module supported elsewhere by the frame 102 of the dissolution test apparatus 100, or as a separate module located external to the frame 102. The pump assembly may include separate pumps for each media dispensing line and/or for each media aspirating line. The pumps may be of any suitable design, one example being the peristaltic type. The media dispensing cannulas 118 and the media aspirating cannulas 120 may constitute the distal end sections of corresponding fluid lines and may have any suitable configuration for dispensing or aspirating liquid (e.g., tubes, hollow probes, nozzles, etc.). In the present context, the term "cannula" simply designates a small liquid conduit of any form that is insertable into a vessel 110.

In a typical operation, each vessel 110 is filled with a predetermined volume of dissolution media by pumping media to the media dispensing cannulas 118 from a suitable media reservoir or other source (not shown). One of the vessels 110 may be utilized as a blank vessel and another as a standard vessel in accordance with known dissolution testing procedures. Dosage units are dropped either manually or automatically into one or more selected media-containing vessels 110, and each stifling element 114 (or other agitation or USP-type device) is rotated within its vessel 110 at a predetermined rate and duration within the test solution as the dosage units dissolve. In other types of tests, a cylindrical basket or cylinder (not shown) loaded with a dosage unit is substituted for each stifling element 114 and rotates or reciprocates within the test solution. For any given vessel 110, the temperature of the media may be maintained at a prescribed temperature (e.g., approximately 37+/−0.5° C.) if certain USP dissolution methods are being conducted. The mixing speed of the stifling element 114 may also be maintained for similar purposes. Media temperature is maintained by immersion of each vessel 110 in the water bath of water bath container 108, or alternatively by direct heating as described previously. The various operative components 114, 118, 120, 122 provided may operate continuously in the vessels 110 during test runs. Alternatively, the operative components 114, 118, 120, 122 may be lowered manually or by an automated assembly 104 or 138 into the corresponding vessels 110, left to remain in the vessels 110 only while sample measurements are being taken at allotted times, and at all other times kept outside of the media contained in the vessels 110. In some implementations, submerging the operative components 114, 118, 120, 122 in the vessel media at intervals may reduce adverse effects attributed to the presence of the operative components 114, 118, 120, 122 within the vessels 110. During a dissolution test, sample aliquots of media may be pumped from the vessels 110 via the media aspiration cannulas 120 and conducted to an analyzing device (not shown) such as, for example, a spectrophotometer to measure analyte concentration from which dissolution rate data may be generated. In some procedures, the samples taken from the vessels 110 are then returned to the vessels 110 via the media dispensing cannulas 118 or separate media return conduits. Alternatively, sample concentration may be measured directly in the vessels 110 by providing fiber-optic probes as appreciated by persons skilled in the art. After a dissolution test is completed, the media contained in the vessels 110 may be removed via the media aspiration cannulas 120 or separate media removal conduits.

Figure 2:
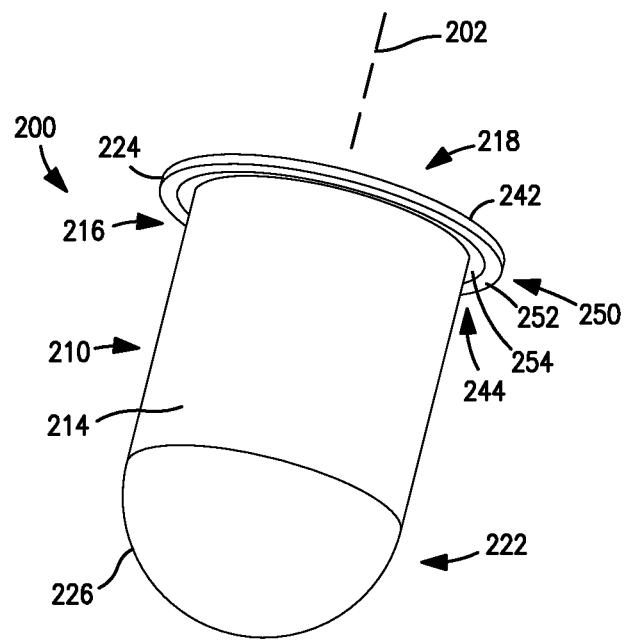
FIG. 2 is a perspective view of an example of a vessel according an implementation taught in the present disclosure.
Figure 3:
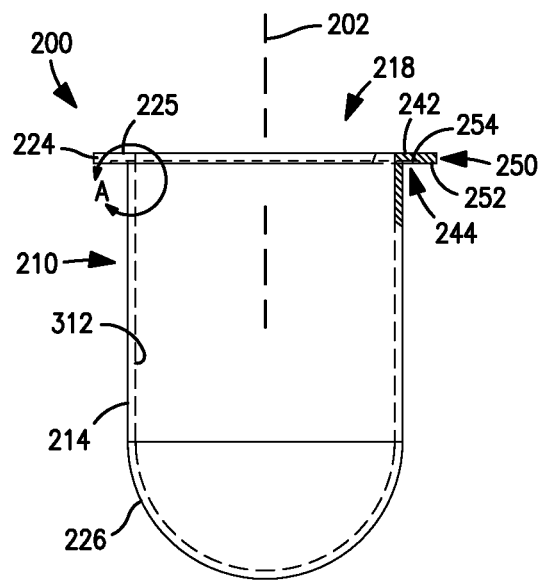
FIG. 3 is an elevation view of the vessel illustrated in FIG. 2.

FIGS. 2 and 3 are respective perspective and elevation views of an example of a vessel 200 with integral verticality control that may be operatively installed in a dissolution test apparatus such as described above and illustrated in FIG. 1. The vessel 200 is symmetrical about a central axis 202. The vessel 200 includes a cylindrical section 210 coaxially disposed about the central axis 202. The cylindrical section 210 includes an inside surface 312 (FIG. 3) facing the interior of the vessel 200 and an opposing outside surface 214. The cylindrical section 210 also generally includes an upper end region 216 at which the cylindrical section 210 circumscribes an upper opening 218 of the vessel 200, and a lower end region 222 axially spaced from the upper end region 216. The vessel 200 further includes an annular flange 224 with a main flange portion 225 that protrudes radially outwardly from the upper end region 216, typically at or proximate to the upper opening 218. The flange 224 includes a top surface 242 and an opposing bottom side 244 generally facing in the direction of the lower end region 222. The vessel 200 also includes a bottom section 226 adjoining the cylindrical section 210 at the lower end region 222. The bottom section 226 may be generally hemispherical as illustrated or may have an alternate shape. For example, the bottom section 226 may be flat, dimpled, or have a peak extending upwardly into the interior of the vessel 200.

As also illustrated in FIGS. 2 and 3, the vessel 200 further includes a ring 250 protruding axially downward from the bottom side 244 of the flange 224. The ring 250 includes a bottom surface 252 facing downward and axially spaced from the main flange portion 225. The ring 250 is concentric with the inside surface 312 of the vessel 200 relative to the central axis 202. In the illustrated example, the ring 250 and its bottom surface 252 are radially spaced from the outside surface 214 of the vessel 200. The annular gap between the ring 250 and the outside surface 214 may be characterized as a groove or channel 254, which may be considered as being part of the bottom surface 244 of the flange 224.

According to the present teachings, the bottom surface 252 is precisely machined so as to be flat and perpendicular to the inside vessel surface 312. The accuracy of the flatness and perpendicularity of the bottom surface 252 ensures that the vessel 200, including its central axis 202 and inside vessel surface 312, is precisely vertical when the flange 224 of the vessel 200 is mounted on a horizontal surface of a vessel supporting structure such as may be provided as part of a dissolution test apparatus or other instrument. In other words, the bottom surface 252 is flat to a very high degree of accuracy or precision, such that the entirety of the bottom surface 252 lies in a horizontal plane. In one example, considering a horizontal plane that is exactly perpendicular to the central axis 202 or the inside vessel surface 312, the bottom surface 252 is coplanar with the horizontal plane to within an accuracy of ±0.020°. This generally means that the maximum amount by which any part of the bottom surface 252 deviates (e.g, projects above or below, or tilts) from the horizontal plane is 0.020°.

Figure 4:
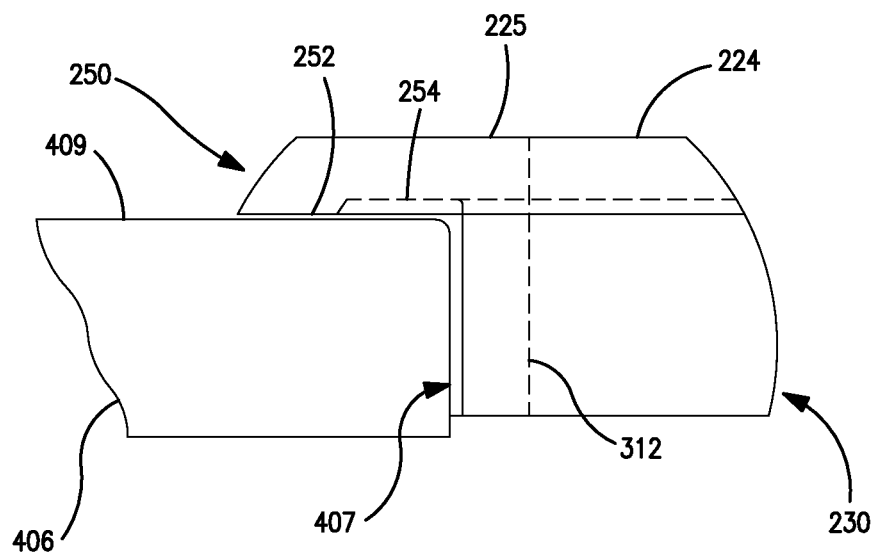
FIG. 4 is a detailed elevation view of the region of the vessel designated "A" in FIG. 3.

FIG. 4 is a detailed elevation view of the region of the vessel 200 designated A in FIG. 3 that includes the ring 250. FIG. 4 also illustrates the interface between the vessel 200 and a vessel support member (or vessel mounting member, or vessel locating member) 406 at which the vessel 200 is mounted. As noted earlier, the vessel support member 406 includes one or more vessel mounting sites at which a like number of vessels may be mounted. At each vessel mounting site, an inside edge or wall 407 of the vessel support member 406 defines an aperture through which the vessel 200 extends. The flange 224 of the vessel 200 extends over a top surface 409 of the vessel support member 406 at the periphery of the aperture. The bottom surface 252 of the ring 250 rests directly on the top surface 409 whereby the vessel support member 406 supports the weight of the vessel 200 and any liquid contained therein.

Figure 5:
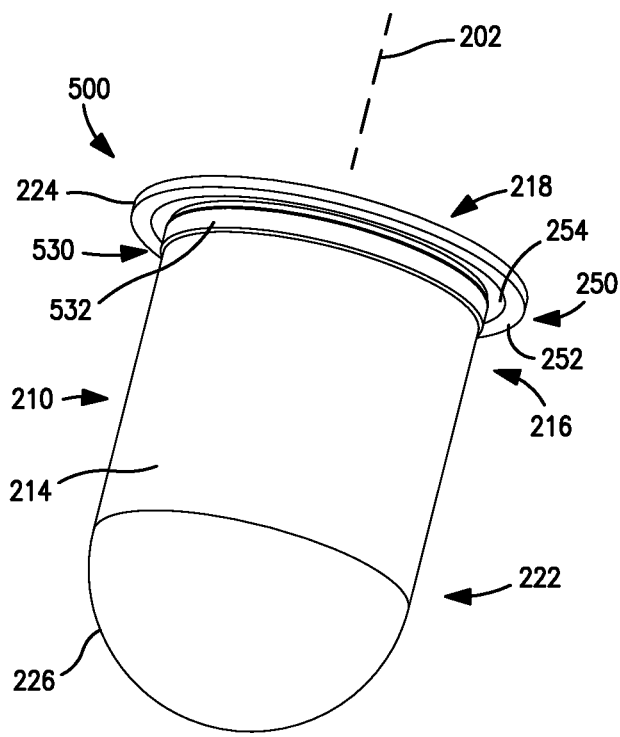
FIG. 5 is a perspective view of an example of a vessel according to another implementation taught in the present disclosure.
Figure 6:
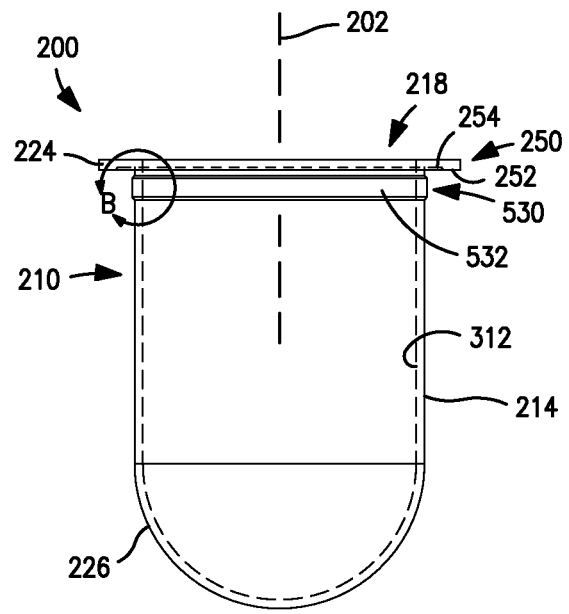
FIG. 6 is an elevation view of the vessel illustrated in FIG. 5.

FIGS. 5 and 6 are respective perspective and elevation views of a vessel 500 according to another implementation that provides both verticality and centering control. The vessel 500 in many respects may be the same or similar to the vessel 200 illustrated in FIGS. 2-4. Accordingly, the vessel 500 includes a cylindrical section 210 coaxially disposed about a central axis 202. The cylindrical section 210 includes an inside surface 312 (FIG. 6), an opposing outside surface 214, an upper end region 216 surrounding an upper opening 218 of the vessel 500, and a lower end region 222. The vessel 500 further includes an annular flange 224 and a bottom section 226 adjoining the cylindrical section 210 at the lower end region 222. The vessel 200 further includes a ring 250 protruding axially downward from the flange 224. The ring 250 includes a bottom surface 252 facing downward. The ring 250 and its bottom surface 252 may be radially spaced from the outside surface 214 of the vessel 200 by an annular gap, groove or channel 254.

As also illustrated in FIGS. 5 and 6, the vessel 500 further includes an annular shoulder 530 protruding radially outward from the outside surface 214 of the cylindrical section 210. Relative to the central axis 202, the shoulder 530 is located axially between the flange 224 (or the upper opening 218 of the vessel 200) and the lower end region 222 of the cylindrical section 210. The shoulder 530 includes an outside shoulder surface 532 that faces radially away from the central axis 202. The shoulder 530 is precisely concentric with the inside surface 312 of the vessel 500 relative to the central axis 202.

Figure 7:
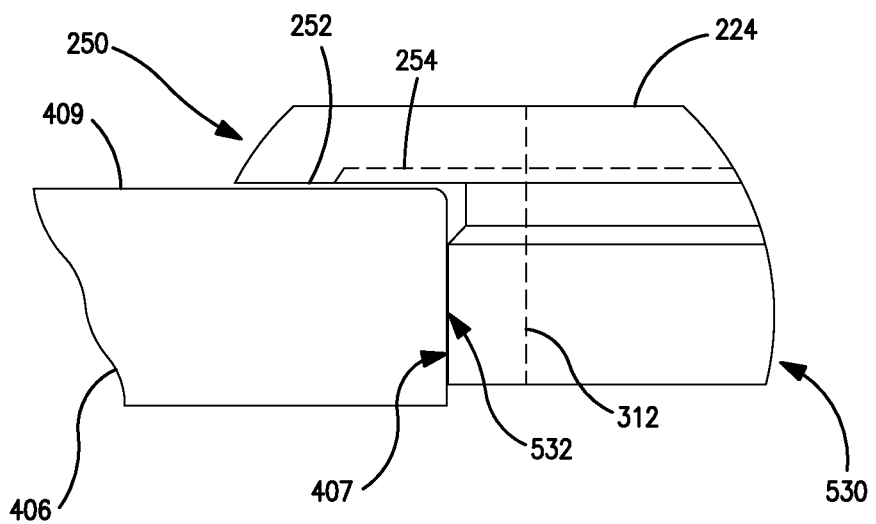
FIG. 7 is a detailed elevation view of the region of the vessel designated "B" in FIG. 6.

FIG. 7 is a detailed elevation view of the region of the vessel 500 designated B in FIG. 6 that includes the ring 250 and the shoulder 530. The interface between the ring 250 and a vessel support member 406 at which the vessel 500 is mounted may be as described earlier in this disclosure. Additionally in the present example, the concentric outside shoulder surface 532 of the vessel 500 directly abuts the inside edge 407 of the aperture. Due to the uniformity or accuracy of this concentricity, the closeness of the fit between the outside shoulder surface 532 and the inside edge 407 is maintained over the entire circumference of the interface. The concentricity is further enhanced by the verticality provided by the accuracy of the ring 250. This configuration ensures that the vessel 500 upon installation is centered in the aperture. No additional components associated with the vessel 500 or the vessel support member 406, or alignment tools or fixtures, are required to center the vessel 500.

Figure 8:
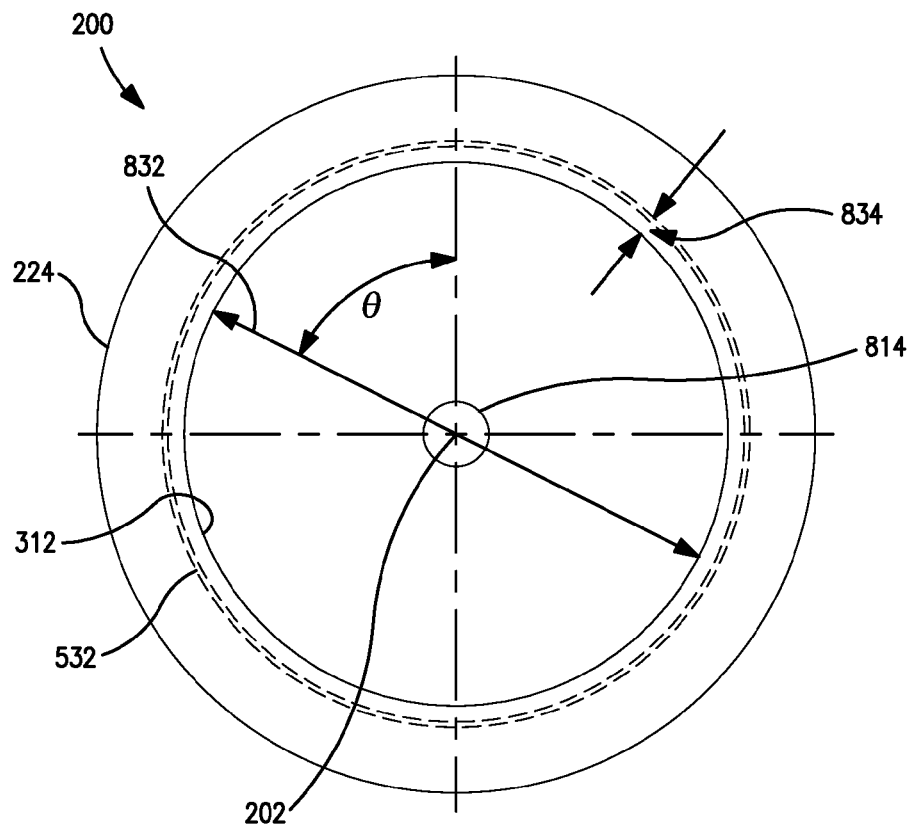
FIG. 8 is a top plan view of the vessel illustrated in FIGS. 5 and 6.

FIG. 8 is a top plan view of the vessel 500 and demonstrates the concentricity of the outside shoulder surface 532 and the inside vessel surface 312. This concentricity is uniform at all circumferential points relative to the central axis 202. That is, as one moves along a reference circumference (for example, the outside shoulder surface 532 or the inside vessel surface 312) at polar angles θ from 0° to 360°, the concentricity is maintained. The uniformity or preciseness of the concentricity ensures that when the vessel 500 is mounted at a vessel plate with a properly dimensioned aperture, the vessel 500 is completely centered at any polar angle. In other words, both the inside vessel surface 312 and the outside shoulder surface 532 are concentric relative to the central axis 202 at any circumferential position at which the vessel 500 may have been installed in the aperture of the vessel plate. The vessel 500 will likewise be centered relative to the aperture of the vessel plate. Stated differently, the central axis 202 of the vessel 500 will be coaxial or collinear with the central axis of the aperture. Moreover, if an elongated structure 814 such as the shaft of an instrument to be operated within the vessel 500 (for example, a paddle- or basket-type instrument) is inserted along the central axis 202 of the vessel 500, the concentricity of both the inside vessel surface 312 and the outside shoulder surface 532 relative to the elongated structure 814 will also be uniform. Moreover, as noted above the quality of the concentricity and alignment of components is further enhanced by the verticality provided by the ring 250.

One way of expressing the uniformity or preciseness of the above-described concentricity is to consider the diametric difference between the inside diameter of the vessel 500 and the outside diameter of the shoulder 530. In FIG. 5, the inside diameter of the vessel 500 as defined by the inside vessel surface 312 is indicated at 832. The outside shoulder surface 532 defines the outside diameter of the shoulder 530. The diametric difference is indicated at 834. In one example, the diametric difference 834 varies or deviates (i.e., the tolerance) by an amount +/−0.05 inch (50 mils) around any referential circumference (i.e., as one moves along polar angles θ from 0° to 360°). In another example, the diametric difference 834 varies by +/−0.01 inch (10 mils). In another example, the diametric difference 834 varies by +/−0.005 inch (5 mils).

In a typical implementation, the vessel 500 (or 200) is fabricated from a glass material having a composition suitable for dissolution testing or other analytical techniques as appreciated by persons skilled in the art. In a typical implementation, the ring 250 is integrally formed with the flange 224, and the flange 224 and the shoulder 530 (if provided) are integrally formed with the cylindrical section 210 of the vessel 500. In one implementation, the ring 250 is formed by building up material at the location of the ring 250, and the shoulder 530 is formed by building up material at the location of the shoulder 530, during fabrication of the vessel 500. A lathe or other suitable tool may then be mounted to the vessel 500 such that the cutting element of the lathe can be moved in desired directions relative to the vessel 500. The lathe is employed to grind or cut the ring material down to form the bottom surface 252 having the desired flatness and perpendicularity to the inside vessel surface 312. Likewise, the lathe is employed to grind or cut the shoulder material down to form the outside shoulder surface 532 having the desired outside diameter and accurate concentricity with the inside vessel surface 312. Laser inspection or other suitable techniques may be employed to verify the accuracy of the geometry and dimensions of the ring 250, the shoulder 530, and other features of the vessel 500.

Figure 9:
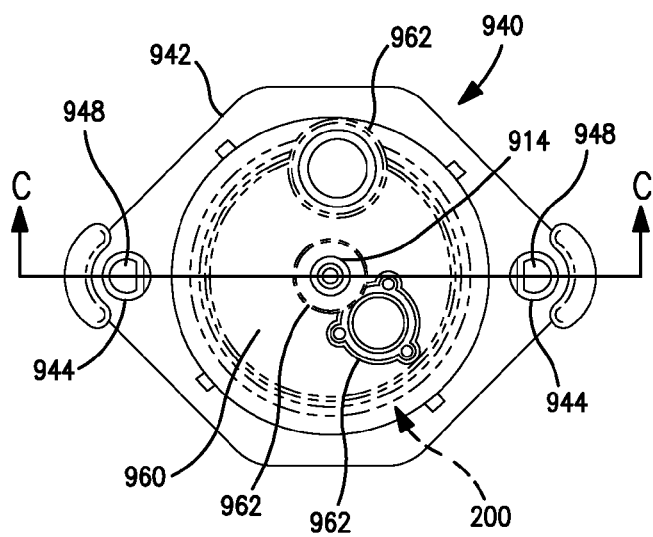
FIG. 9 is a top plan view of a vessel provided with a retention member and a vessel cover according to implementations taught in the present disclosure.
Figure 10:
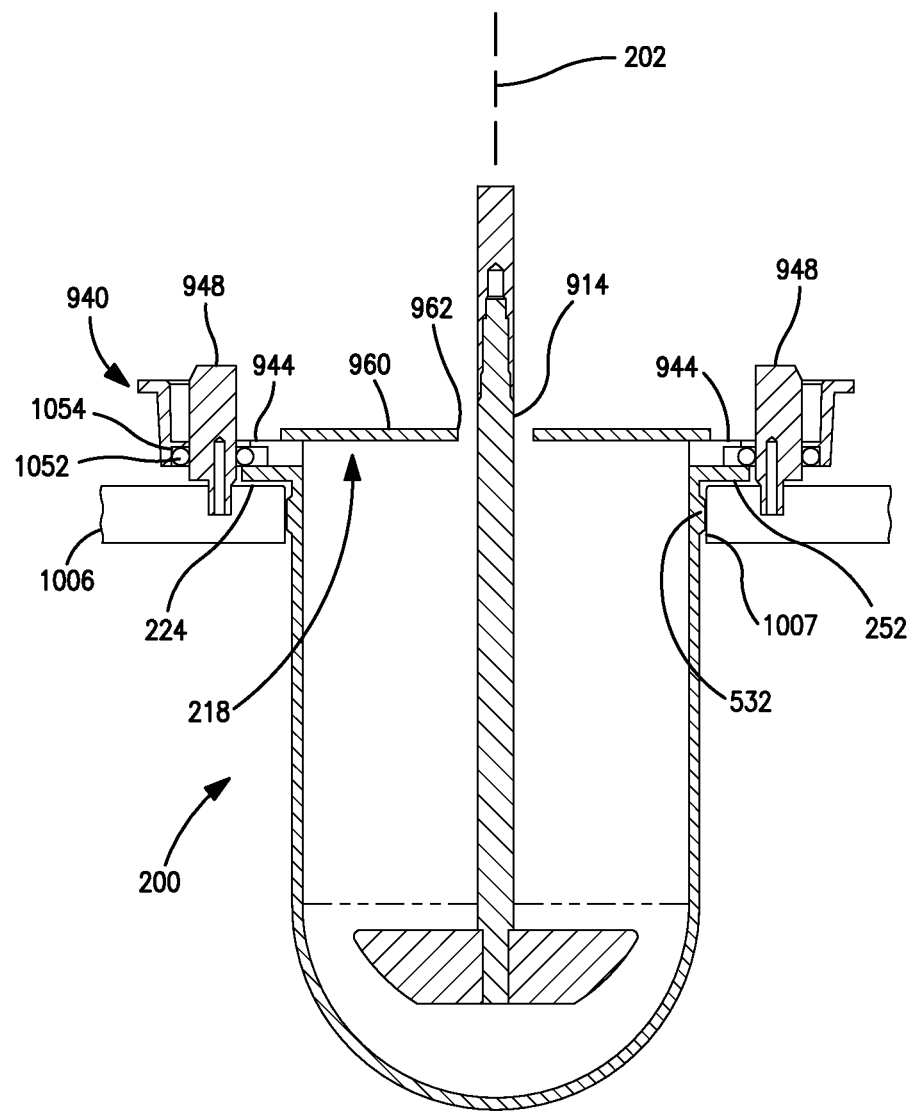
FIG. 10 is a cut-away elevation view of the vessel illustrated in FIG. 9, taken along line "C-C".

FIG. 9 is a top view of a self-centering vessel 500 as described above. FIG. 10 is a cross-sectional elevation view of the vessel 500 taken along line C-C in FIG. 9. It will be understood that the following discussion regarding FIGS. 9 and 10 also applies to the vessel 200 described earlier in this disclosure. The vessel 500 is mounted at a vessel support member 1006 (FIG. 10) at a vertical position at which an inside edge 1007 of the vessel support member 1006 defining the aperture directly abuts the outside shoulder surface 532 of the vessel. Optionally, a retention member 940 is provided with the vessel 500. The retention member 940 may have any configuration suitable for retaining the vessel 500 in its operative mounted position in the aperture of the vessel support member 1006 to prevent the vessel 500 from moving vertically out from the aperture after the vessel 500 has been properly installed. The retention member 940 is therefore particularly useful in conjunction with the use of a liquid bath as described above and illustrated in FIG. 1, as the retention member 940 prevents the vessel 500 from "popping out" of the aperture due to buoyancy effects. In the non-limiting example illustrated in FIGS. 9 and 10, the retention member 940 may include an annular or ring-shaped portion 942 having an aperture coaxial with the central axis 202 of the vessel 500, and one or more holes 944 radially offset from the central axis 202. After lowering a vessel 500 through the aperture of the vessel support member 1006, the retention member 940 is lowered onto the flange 224 of the vessel 500 such that posts or pins 948 affixed to the vessel support member 1006 extend through the holes 944. O-rings 1052 are provided in annular recesses or grooves 1054 of the retention member 940 that are aligned with the holes 944 and located between the holes 944 and the flange 224 of the vessel 500. The frictional contact between the o-rings 1052 and the pins 948 is sufficient to lock or retain the vessel 500 in place vertically at the vessel mounting site.

FIGS. 9 and 10 also illustrate an optional vessel cover 960 that may be employed to span the upper opening 218 of the vessel 500 to minimize loss of media via evaporation. Such a vessel cover 960 may be supported directly on the flange 224 of the vessel 500. Alternatively, in a case where a retention member 940 is utilized, the vessel cover 960 may be supported by the retention member 940. As shown in FIG. 9, the vessel cover 960 may have one or more apertures 962 to accommodate the use of in situ operative components such as a shaft 914 or other component described earlier in the present disclosure.

Figure 11:
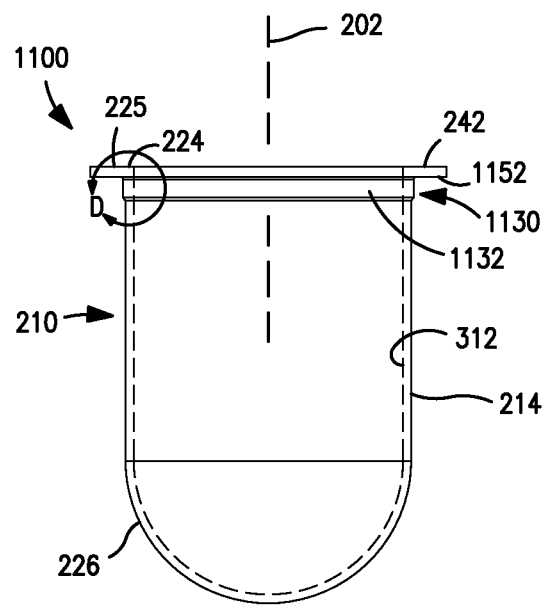
FIG. 11 is an elevation view of another example of a vessel as taught in the present disclosure.
Figure 12:
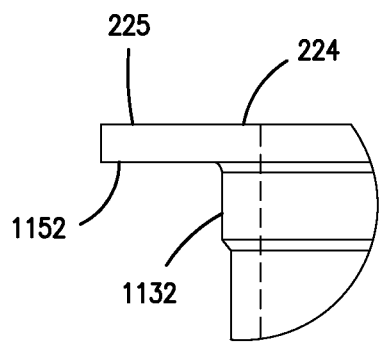
FIG. 12 is a detailed elevation view of the region of the vessel designated "D" in FIG. 11.

FIG. 11 is an elevation view of another example of a vessel 1100 with integral verticality control as taught in the present disclosure. FIG. 12 is a detailed elevation view of the region of the vessel 1100 designated "D" in FIG. 11. As in previous examples, the vessel 1100 further includes an annular flange 224 with a main flange portion 225 that protrudes radially outwardly from the upper end region 216. In the present example, a bottom surface 1152 faces downward and is located directly at the underside of the main flange portion 225 without an intervening ring 250 (compare with FIGS. 2-7). As in previous examples, the bottom surface 1152 is precisely machined so as to be flat and perpendicular to the inside vessel surface 312. The accuracy of the flatness and perpendicularity of the bottom surface 1152 ensures that the vessel 1100, including its central axis 202 and inside vessel surface 312, is precisely vertical when the flange 224 of the vessel 1100 is mounted on a horizontal surface of a vessel supporting structure. The bottom surface 1152 is flat to a very high degree of accuracy or precision, such that the entirety of the bottom surface 1152 lies in a horizontal plane. In one example, considering a horizontal plane that is exactly perpendicular to the central axis 202 or the inside vessel surface 312, the bottom surface 1152 is coplanar with the horizontal plane to within an accuracy of ±0.020°. This generally means that the maximum amount by which any part of the bottom surface 1152 deviates (e.g, projects above or below, or tilts) from the horizontal plane is 0.020°. The vessel 1100 in this example also provides centering control. Accordingly, the vessel 1100 includes an annular shoulder 1130 protruding radially outward from the outside surface 214 of the cylindrical section 210. Similar to the example illustrated in FIGS. 5-7, relative to the central axis 202 the shoulder 1130 is located axially between the flange 224 (or the upper opening 218 of the vessel 200) and the lower end region 222 of the cylindrical section 210. The shoulder 1130 includes an outside shoulder surface 1132 that faces radially away from the central axis 202. The shoulder 1130 is precisely concentric with the inside surface 312 of the vessel 1100 relative to the central axis 202. In the present example, however, the shoulder 1130 is integrally adjoined to the flange 224 at its bottom surface 1152. The shoulder 1130 provides advantages as described above for the previous example, including providing a uniform concentricity and diametric difference as described above in conjunction with FIG. 8. The integrated flange 224 and shoulder 1130 may be precisely fabricated and the precision verified in the manner described above for the previous examples.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A vessel comprising:
a cylindrical section coaxially disposed about a central axis of the vessel, the cylindrical section comprising an inside vessel surface, an outside vessel surface opposing the inside vessel surface, an upper end region circumscribing a vessel opening, and a lower end region axially spaced from the upper end region;
a bottom section disposed at the lower end region;
a flange coaxially disposed about the central axis, the flange comprising a main flange portion extending radially outward from the outside vessel surface at the upper end region, and a bottom surface facing generally toward the lower end region and perpendicular to the inside vessel surface, wherein the bottom surface lies in a horizontal plane and is entirely coplanar with the horizontal plane; and
a shoulder coaxially disposed about the central axis in the upper end region, the shoulder extending radially outward from the outside vessel surface and located axially between the flange and the lower end region, the shoulder comprising an outside shoulder surface concentric with the inside vessel surface relative to the central axis.

2. The vessel of claim 1, wherein the central axis is a vertical axis, and the bottom surface is entirely coplanar with the horizontal plane to within an accuracy of ±0.020°.

3. The vessel of claim 1, further comprising a ring coaxially disposed about the central axis and extending axially downward from the main flange portion, the ring terminating at a ring bottom surface wherein the ring bottom surface is axially distant from the main flange portion.

4. The vessel of claim 3, wherein the ring is radially spaced from the outside vessel surface by an annular groove formed in the flange.

5. The vessel of claim 1, wherein the shoulder is spaced from the flange.

6. The vessel of claim 1, wherein the inside vessel surface defines an inside vessel diameter of the cylindrical section, the outside shoulder surface defines an outside shoulder diameter of the shoulder, and the diametric difference between the inside vessel diameter and the outside shoulder diameter is uniform at any circumferential point relative to the central axis.

7. The vessel of claim 1, wherein the inside vessel surface defines an inside vessel diameter of the cylindrical section, the outside shoulder surface defines an outside shoulder diameter of the shoulder, and the diametric difference between the inside vessel diameter and the outside shoulder diameter varies by no greater than +/−0.05 inch at any circumferential point relative to the central axis.

8. The vessel of claim 1, wherein the shoulder integrally adjoins the flange.

9. A dissolution test apparatus comprising:
a vessel support member comprising a top surface and an inside edge circumscribing an aperture; and
a vessel extending through the aperture and comprising:
a cylindrical section coaxially disposed about a central axis of the vessel, the cylindrical section comprising an inside vessel surface, an outside vessel surface opposing the inside vessel surface, an upper end region circumscribing a vessel opening, and a lower end region axially spaced from the upper end region;
a bottom section disposed at the lower end region;
a flange coaxially disposed about the central axis, the flange comprising a main flange portion extending radially outward from the outside vessel surface at the upper end region, and a bottom surface facing generally toward the lower end region and perpendicular to the inside vessel surface, wherein the bottom surface lies in a horizontal plane and is entirely coplanar with the horizontal plane, wherein the inside vessel surface is parallel to the inside edge of the vessel support member; and
a shoulder coaxially disposed about the central axis in the upper end region, the shoulder extending radially outward from the outside vessel surface and located axially between the flange and the lower end region, the shoulder comprising an outside shoulder surface concentric with the inside vessel surface relative to the central axis, the outside shoulder surface abutting the inside edge of the aperture.

10. The dissolution test apparatus of claim 9, wherein the vessel further comprises a ring coaxially disposed about the central axis and extending axially downward from the main flange portion, the ring terminating at the bottom surface wherein the bottom surface is axially distant from the main flange portion.

11. The dissolution test apparatus of claim 10, wherein the ring is radially spaced from the outside vessel surface by an annular groove formed in the flange.

12. The dissolution test apparatus of claim 9, wherein the shoulder is spaced from the flange.

13. The dissolution test apparatus of claim 12, wherein the inside vessel surface defines an inside vessel diameter of the cylindrical section, the outside shoulder surface defines an outside shoulder diameter of the shoulder, and the diametric difference between the inside vessel diameter and the outside shoulder diameter is uniform at any circumferential point relative to the central axis.

14. The dissolution test apparatus of claim 13, further comprising an elongated structure extending into the vessel, wherein the outside shoulder surface and the inside vessel surface are concentric with the elongated structure.

15. The dissolution test apparatus of claim 9, wherein the shoulder integrally adjoins the flange.

16. The dissolution test apparatus of claim 9, further comprising an elongated structure extending into the vessel, wherein the inside vessel surface is parallel with the elongated structure.

17. A method for centering a vessel in an aperture of a vessel support member of a dissolution test apparatus, the aperture being coaxial with a vertical axis running through a center of the aperture, the method comprising:
  inserting the vessel through the aperture, the vessel comprising an inside vessel surface coaxially disposed about a central axis of the vessel, an outside vessel surface, a flange extending radially outward from the outside vessel surface, and a bottom surface extending axially downward from the flange and perpendicular to the inside vessel surface, wherein the vessel further comprises an annular shoulder protruding radially outward from the outside vessel surface, the annular shoulder comprising an outside shoulder surface concentric with the inside vessel surface relative to the central axis; and
  supporting the vessel in a vertical orientation relative to the aperture by placing the bottom surface on a top surface of the vessel support member, wherein the entire inside vessel surface is parallel with the vertical axis.

18. The method of claim 17, further comprising inserting an elongated structure into the vessel, wherein the inside vessel surface is parallel with the elongated structure.

19. The method of claim 17, further comprising fixing the position of the vessel relative to the aperture at an elevation at which the outside shoulder surface abuts an inside edge of the vessel support member circumscribing the aperture, wherein the central axis of the vessel is aligned with the vertical axis at any polar position relative to the vertical axis.

20. The method of claim 19, further comprising inserting an elongated structure into the vessel, wherein the outside shoulder surface and the inside vessel surface are concentric with the elongated structure.

* * * * *